United States Patent [19]

Fastritsky et al.

[11] Patent Number: 4,503,392

[45] Date of Patent: Mar. 5, 1985

[54] APPARATUS FOR NON-DESTRUCTIVE TESTING OF SPOT WELDS USING AN ELECTROMAGNETIC FIELD

[75] Inventors: Viktor S. Fastritsky; Laimonis T. Vingris, both of Riga; Vasily V. Ardentov; Jury B. Florinsky, both of Leningrad; Viktor I. Plotnikov, Tolyatti; Leonid A. Rodnevsky, Tolyatti; Gennady N. Alexeev, Tolyatti, all of U.S.S.R.

[73] Assignee: Rizhsky Politekhnichesky Institut, Riga, U.S.S.R.

[21] Appl. No.: 285,556

[22] Filed: Jul. 21, 1981

[51] Int. Cl.³ .................... G01N 27/82; G01N 27/90; G01R 33/12

[52] U.S. Cl. .................................. 324/232; 324/233; 324/238

[58] Field of Search .................. 324/232, 228–230, 324/233–238, 239, 240

[56] References Cited

U.S. PATENT DOCUMENTS

| 2,900,595 | 8/1959 | Mengel et al. | 324/335 |
| 3,526,829 | 9/1978 | Noble | 324/238 |
| 4,287,474 | 9/1981 | Fastritsky et al. | 324/233 |

FOREIGN PATENT DOCUMENTS 2004069  3/1979  United Kingdom ............... 324/232

OTHER PUBLICATIONS

Renken et al., "Status Report in Eddy Current Theory and Application", Argonne National Laboratory Report-ANL-5861, Nov. 1958, pp. 1-7 and 37-48.

Primary Examiner—Gerard R. Strecker
Assistant Examiner—Warren S. Edmonds
Attorney, Agent, or Firm—Fleit, Jacobson, Cohn & Price

[57] ABSTRACT

A method of and apparatus for nondestructive testing of spot welds by producing in a test weld high and low frequency electromagnetic fields to induce eddy currents in the weld zone. The difference between the phase values of the resultant electromagnetic field intensities is indicative of the quality of the weld. The apparatus includes an eddy current transducer, high and low-frequency measuring channels, an indicator, and a controlled commutator for alternate connection of the eddy current transducer to the low-frequency measuring channel or to the high-frequency measuring channel. A memory unit is provided for storing the output signal of the high-frequency measuring channel, and a comparator is provided for comparing the signal stored in the memory unit with the output signal of the low-frequency measuring channel. A control unit alternately generates signals for simultaneously connecting the eddy current transducer to the high-frequency measuring channel and for storing the output signal of the high-frequency measuring channel in the memory unit, and signals for simultaneously connecting the eddy current transducer to the low-frequency measuring channel, and for comparing the signal of the low-frequency measuring channel with the signal stored in the memory unit.

2 Claims, 7 Drawing Figures

APPARATUS FOR NON-DESTRUCTIVE TESTING OF SPOT WELDS USING AN ELECTROMAGNETIC FIELD

FIELD OF THE INVENTION

The present invention relates to the field of weld testing, and more particularly to methods of and apparatus for nondestructive testing of spot welds.

The present invention can be most advantageously used in machine, shipbuilding, aircraft, and automotive industries for flaw detection and nondestructive evaluation of properties of various metal structures.

BACKGROUND OF THE INVENTION

Spot welding is of wide application for joining part. For example, a car has over 22,000 spot welds. However, the use of spot welding in critical parts is impossible without a reliable method of and apparatus for evaluating the quality of the nugget of a spot weld.

Known in the art is a method of nondestructive testing of spot welds, residing in that the test weld is examined by X-rays which are non-uniformly absorbed by various regions of the weld nugget because of inhomogeneity of its chemical composition. X-rays penetrate through the test weld and fall onto an X-ray film, whereon, after development, liquation rings are formed, the diameter of the weld nugget being evaluated from the dimensions of said rings.

The apparatus realizing this method comprises an X-ray source and a detector, e.g. X-ray film on which X-rays having passed through the test weld are recorded.

The abovementioned method of and apparatus for nondestructive testing of spot welds suffer from the disadvantage residing in that it is impossible to detect such a dangerous and popular welding effect as the lack of fusion for materials which do not exibit sharply defined inhomogeneity of chemical composition in the weld nugget section.

Besides, said method and apparatus have a low efficiency and are of high cost.

It is possible to improve the efficiency of the method and to reduce the cost of the equipment by the use of an eddy current method of spot weld testing based on the fact that the nugget of the test spot weld and a welded material outside the nugget zone possess different conductivities.

The apparatus based on the eddy current method of testing should provide a means for tuning out from the interfering effect of variations of the lift-off formed between a superimposed eddy-current transducer and a test weld due to an indentation left by electrodes in the spot weld zone, tuning out from the effect of local inhomogeneity of a test weld in its chemical composition, tuning out from the action of temperature of the test weld, and tuning out the action caused by variation in the structure of the test weld material as a result of their mechanical treatment.

There is well known and widely used a method of nondestructive testing of spot welds, residing in that a primary electromagnetic field is produced in the test weld zone, which field induces in said zone eddy currents generating a secondary field, whereupon a phase value of the resultant electromagnetic field intensity is determined, and the presence and quality of the weld nugget are evaluated in accordance with said values.

The apparatus realizing this method of nondestructive testing of spot welds comprises a sinusoidal oscillator, a reference channel connected to one of the outputs of the oscillator and representing a phase shifter having its output connected to one of the inputs of a phase meter, and a measuring channel connected to the other output of the oscillator and representing an unbalanced bridge circuit with a superimposed eddy-current transducer included into one of its arms and with its output connected to the other input of the phase meter.

The output voltage of the sinusoidal oscillator is supplied to the phase shifter which serves to set the phase of the reference voltage and to the bridge circuit with one of its arms including the eddy current transducer placed upon a test weld. The transducer complex resistance and hence the output signal of the bridge circuit wherein the transducer is included vary according to the weld quality. The bridge circuit is adjusted so that the phase of the output voltage is independent of the lift-off between the superimposed transducer and the article to be tested and is determined only by variations in the electric conductivity of the tested zone, which in turn is dependent upon the weld quality. From the output of the phase shifter the signal is supplied to one of the inputs of the phase meter, and from the output of the bridge circuit it is fed to the second input of the phase meter. The transducer being placed upon the reference weld, the phase of the reference voltage is changed by means of the phase shifter so that the phase shift between the reference and measured voltages, in case of a quality weld, should be equal to zero. Thereupon, the transducer is placed upon the test weld, and the weld quality is evaluated according to indications of the phase meter.

The abovementioned method of and apparatus for nondestructive testing of spot welds make it possible to tune out from the interfering effect of variations in the lift-off between the superimposed eddy-current transducer and the test weld only in those cases when phase of the output voltage of the unbalanced bridge circuit is approximately linearly dependent upon the conductivity of the test weld material and upon the size of the lift-off. As soon as this linear dependence is distorted, it becomes practically impossible to tune out completely from the effect of variations in the lift-off size, as a result of which the phase of the output voltage of the unbalanced bridge circuit will also depend upon the lift-off value.

This method of and apparatus for nondestructive testing of spot welds do not permit to find out unambiguously whether the conductivity of the test weld material has changed, as compared to that of the reference weld material, due to a quality welding or under the influence of undesirable factors, such as:
 local inhomogeneity of the test weld material in its chemical composition,
 variations in the ambient temperature, and
 variations in the structure of the test weld material as a result of its mechanical treatment.

What is more, this method of nondestructive testing of spot welds and the apparatus implementing the same make it possible to evaluate the weld nugget zone only dependently upon the change in its one parameter, namely upon the change in electrical conductivity of the weld nugget zone material. This results in that the reliability of the test is declined.

Besides, the apparatus must be preadjusted by placing the eddy-current transducer upon the reference weld.

However, for a number of materials, such as aluminum-magnesium alloys, a reference weld cannot be revealed by nondestructive methods.

Known in the art is a method of nondestructive testing of spot welds (Cf. U.S. Pat. No. 3,526,829), residing in that two pulsed electromagnetic fields are produced, which are locally applied to the test weld and to the reference weld. Thereupon, the depth of penetration of two pulsed electromagnetic fields into the welds is determined by dynamic impedance measurements of the effect of the induced eddy currents on the applied electromagnetic fields.

The apparatus realizing this method comprises eddy current transducers placed upon the reference and test welds, an impedance comparator having its inputs connected to the eddy current transducers, and a controlled switch having its output connected to a stored energy source. The output of the comparator is connected to a threshold circuit having its output connected to an information display unit wherein an information signal varying in accordance with the difference between the measured impedance values in the reference and in the test welds is displayed in an acceptance-rejection form.

By means of this method and the apparatus it is possible to test spot welds of small thickness.

Simultaneous measurements of electromagnetic parameters of the test weld and reference weld and comparison of the results of such measurements make it possible to eliminate to some extent the interfering effect of ambient temperature, assuming that the temperatures of the test weld and of the reference weld are equal.

However, this method of and apparatus for nondestructive testing of spot welds are rather difficult to be applied to the welding of materials having substantial variations in physical-and-chemical characteristics within the same brand of materials.

Also known in the prior art is a method of nondestructive testing of spot welds (Cf. USSR Inventor's Certificate No. 336,587), residing in that a superimposed eddy current transducer produces in a test weld nugget zone a primary low-frequency electromagnetic field inducing in said zone eddy currents which produce a secondary low-frequency electromagnetic field. Thereupon, the phase value of the resultant low-frequency electromagnetic field intensity is determined, according to which the quality of the weld nugget zone is evaluated.

The apparatus realizing this method comprises a low-frequency measuring channel including a low-frequency generator, a T-shaped unbalanced LCR bridge circuit connected to the output of the generator, a main eddy current transducer included in the T-shaped bridge as an L element, an electronic indicator of the bridge output signal, a phase shifter, frequency multipliers, and a phase detector which are connected across the output of the generator and the main superimposed eddy current transducer.

Fixed in the center of the main eddy current transducer is an additional eddy current transducer which forms in combination with a capacitor a measuring circuit for measuring the lift-off depth. The measuring circuit of the additional eddy current transducer is connected to a high-frequency generator and to the indicator of the lift-off depth.

Sinusoidal voltage of the low-frequency generator is applied to the input of the T-shaped bridge circuit and to the phase shifter. The bridge circuit is balanced when the main superimposed eddy current transducer is placed on the reference weld. Thereupon, the main eddy current transducer whose parameters vary according to the weld quality is placed upon the test weld, and an error signal dependent upon the weld quality appears at the bridge output.

The amplitude of the error signal is measured by the electronic indicator. To measure the phase, the signal is taken directly from the main superimposed eddy current transducer and applied through the frequency multiplier to the phase meter. A reference voltage is supplied from the low-frequency generator to the phase meter through the phase shifter and frequency multiplier. To determine the lift-off depth, voltage is supplied from the high-frequency generator to the measuring circuit. The signal corresponding to the lift-off depth is supplied from the measuring circuit to the lift-off depth indicator.

This method and apparatus make it possible to perform tuning out from the interfering effect of variations in the lift-off between the superimposed eddy current transducer and the test weld.

However, the aforementioned method and apparatus provide low reliability of testing since they fail to reveal unambiguously whether the conductivity of the test weld material has changed as compared to that of the reference weld material due to a quality weld or under the influence of undesirable factors, such as:
  local inhomogeneity in chemical composition of the test weld material,
  variations in the ambient temperature, and
  variations in the structure of the test weld material, caused by its mechanical treatment.

Besides, the use of two superimposed eddy current transducers arranged coaxially considerably increases the overall dimensions of the apparatus.

Also known is a method of nondestructive testing of spot welds (see "Heads of Reports of the Second Higher School Conference on the Problems of Nondestruction Quality Testing", Riga, RPI, 1975. pp. 140–143). According to this method, as a first step calibrating, is performed i.e. dependence of the phase value of intensity of each of the applied frequencies on the metered parameters of the spot weld, namely on the depth of fusion and on the nugget diameter, is determined at standart points thereupon a curve is plotted.

Then a primary low-frequency electromagnetic field is produced in the test weld nugget zone, which field induces in said zone eddy currents generating a secondary low-frequency electromagnetic field which, interacting with the primary low-frequency electromagnetic field, forms a resultant low-frequency electromagnetic field, afterwards the phase value of the resultant low-frequency electromagnetic field intensity is determined. Next, a primary high-frequency electromagnetic field is produced in the test weld nugget zone, which field induces in said zone eddy currents generating a secondary high-frequency electromagnetic field which, interacting with the primary high-frequency electromagnetic field, forms a resultant high-frequency electromagnetic field, afterwards the phase value of the resultant high-frequency electromagnetic field intensity is determined.

The spot weld quality is evaluated using the above curve on which points corresponding to the resultant phase values of intensity of the resultant low-frequency and high-frequency electromagnetic fields are located.

the apparatus realizing this method comprises a superimposed eddy current transducer, a low-frequency measuring channel including a low-frequency generator, an unbalanced bridge circuit, and a phase detector, all elements being connected in series, a high-frequency measuring channel including a high-frequency generator, an unbalanced bridge circuit, and a phase detector, all connected in series, and an indicator.

The above mentioned method and apparatus permit the testing reliability to be increased to some extent, since the spot weld nugget quality is evaluated according to two parameters, namely depth of fusion and diameter of the spot weld nugget zone.

However, said method and apparatus fail to provide a sufficient reliability since the quality of the spot weld nugget is evaluated based on absolute phase values of intensity of the resultant electromagnetic fields.

What is more, said method and apparatus do not permit to find out unambiguously whether the conductivity of the test weld material has changed as compared to that of the reference weld material due to a quality weld or under the influence of undesirable factors such as local inhomogeneity in chemical composition of the test weld material variations in the ambient temperature, and variations in the test weld material structure caused by its mechanical treatment.

SUMMARY OF THE INVENTION

It is an object of the present invention to provide a method of an apparatus for nondestructive testing of spot welds, enabling the reliability of testing to be improved.

Another object of the present invention is to provide a method of and apparatus for nondestructive testing of spot welds, making it possible to perform testing regardless of variations in chemical composition of the material, in the structure of the material caused by its mechanical treatment, and in the environmental conditions, such as an ambient temperature.

Still another object of the present invention is to provide a method of and apparatus for nondestructive testing of spot welds, enabling to perform testing without the need to pre-adjust it on a reference weld.

Yet another object of the present invention is to provide a method of and an apparatus for nondestructive testing of spot welds, enabling the spot welding defects to be classified i.e. to distinguish spot welds having a sticking-type defects from spot welds having defects of through penetration type.

With these and other objects in view, there is provided a method of nondestructive testing of spot welds, comprising the steps of producing in a test weld nugget zone a primary low-frequency electromagnetic field inducing eddy currents in said zone, generating a secondary low-frequency electromagnetic field which, interacting with the primary low-frequency electromagnetic field, forms a resultant low-frequency electromagnetic field, of determining in said zone the phase value of the resultant low-frequency electromagnetic field intensity, of producing in the test weld nugget zone a primary high-frequency electromagnetic field inducing eddy currents in said zone, generating a secondary high-frequency electromagnetic field which interacting with the primary high-frequency electromagnetic field forms a resultant high-frequency electromagnetic field, of determining in said zone the phase value of the resultant high-frequency electromagnetic field intensity, and of evaluating the spot weld nugget quality according to the phase values of intensity of the resultant high-frequency and low-frequency electromagnetic field, wherein, accordng to the invention, a difference between the phase values of the resultant high-frequency electromagnetic field intensity and that of the resultant low-frequency electromagnetic field intensity is determined, and the quality of the weld nugget is evaluated directly from that difference.

Determination of the difference between the phase values of the resultant electromagnetic field intensities provides reliable testing of spot welds even in the presence of interfering factors.

Under the influence of such interfering factors as inconstancy of the material chemical composition of joined parts, variations in the structure of the material in the course of its mechnical treatment, and variations in the ambient temperature, there occur considerable changes in the material conductivity, commensurable with or even greater than those caused by welding.

Since these changes in conductivity, caused by said interfering factors, are practically the same both in the surface layer and in the weld nugget, the difference between the values of conductivities or the difference between the phase values of field intensities respectively proportional to conductivities in these zones, is independent of said interfering factors and is determined only by variations in the structure of the material caused by welding.

It is advisable to produce a primary high-frequency electromagnetic field in a zone disposed in the immediate vicinity to the weld nugget, which field induces eddy currents in said zone, generating a secondary high-frequency electromagnetic field forming, while interacting with the primary high-frequency electromagnetic field a resultant high-frequency electromagnetic field, to determine the difference between the phase value of the intensity of the resultant high-frequency electromagnetic field produced in the zone disposed in the immediate vicinity to the weld nugget and that of the resultant high-frequency electromagnetic field produced in the weld nugget zone, and to evaluate the quality of the spot weld nugget directly from that difference.

Generation of the primary high-frequency electromagnetic field in the zone disposed in the immediate vicinity to the weld nugget makes it possible to induce eddy currents in said zone and to measure the phase value of the resultant high-frequency electromagnetic field intensity in a surface layer not subjected to thermal treatment during the welding process.

In case of the sticking-type defect present in the spot weld, variations in the material structure in the surface layer of the weld joint cause but a little change in its conductivity which only slightly differs from the conductivity of the material subjected to no thermal treatment.

The presence of the through penetration defect is characterized by a substantial variations in the material structure in the surface layer and, consequently, by substantial variations in the material conductivity.

With these and other objects in view, there is also provided an apparatus for nondestructive testing of spot welds, comprising a superimposed eddy current transducer, a low-frequency measuring channel including a low-frequency signal generator, an unbalanced bridge circuit and a phase detector, connected in series, a high-frequency measuring channel including a high-frequency signal generator, an unbalanced bridge circuit and a phase detector, connected in series, and an indicator, which apparatus, according to the invention, further comprises a controlled commutator for alternate connection of the superimposed eddy current transducer to the unbalanced bridge circuits of the low-frequency and high-frequency measuring channels, a memory unit adapted for storage of the output signal of the phase detector of the high-frequency measuring channel and connected to the output of the phase detector of the high-frequency measuring channel, a comparator for comparing the signal stored in the memory unit with the signal of the phase detector of the low-frequency measuring channel, and a control unit having its outputs connected to the control inputs of the controlled commutator, of the memory unit and of the comparator, and which alternately generates signals for simultaneously connecting of the superimposed eddy current transducer to the unbalanced bridge circuit of the high-frequency measuring channel and for storing the output signal of the phase detector of the high-frequency measuring channel in the memory unit, and signals for connecting the superimposed eddy current transducer to the unbalanced bridge circuit of the low-frequency measuring channel and for comparing the signal of the phase detector of the low-frequency measuring channel with the signal stored in the memory unit.

The control unit, controlled commutator, memory unit, and comparator make it possible to determine the difference between the phase values of the intensities of the resultant high-frequency electromagnetic field and the resultant low-frequency electromagnetic field said difference being dependent upon the difference between conductivities of the material in the surface layer of the test weld and in the test weld nugget zone, conditioned only by the process of welding.

It is advisable that the apparatus be further provided with controlled commutator adapted to switch a second input of the comparator from the phase detector of the low-frequency measuring channel and to the phase detector of the high-frequency measuring channel, the control unit being provided with a fourth output connected with a control input of the additional controlled commutator and generating signals to connect simultaneously the superimposed eddy current transducer to the unbalanced bridge circuit of the high-frequency measuring channel, the phase detector of the high-frequency measuring channel to the second input of the comparator, and to compare the signal from the phase detector of the high-frequency measuring channel with the signal stored in the memory unit.

Such an embodiment of the apparatus makes it possible to compare two signals which are proportional to the conductivity of the test weld material in the surface layer in the weld nugget zone and in the surface layer in the zone disposed in immediate vicinity to the weld nugget.

Other objects, features and advantages of the invention will become more apparent upon consideration of the following detailed description of its embodiments taken in conjunction with the accompanying drawings, in which:

DESCRIPTION OF THE PREFERRED EMBODIMENTS

The method of nondestructive testing of spot welds is realized as follows. A superimposed eddy current transducer 1 (FIG. 1) is placed over a test weld 2. To suppress the effect of variations in the lift-off between the superimposed eddy current transducer 1 and the test weld 2, the transducer 1 is included into an unbalanced bridge circuit which is adjusted by a conventional method so that the phase of the output voltage of the unbalanced bridge circuit is independent of the lift-off value between the superimposed eddy current transducer 1 and the test weld 2, and is determined only by variations in the conductivity in a test zone, the variations in conductivity depending upon variations in the structure of a material, i.e. upon the quality of the weld nugget and weld defects present therein.

Figure 1:
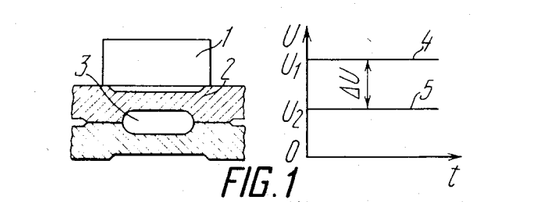
FIG. 1 is a cross-sectional view of a spot weld with a superimposed transducer, and a graph representing the output signal of the superimposed eddy current transducer versus the time over which testing is performed, according to the invention.

By means of the superimposed eddy current transducer 1 powered by a sinusoidal high-frequency voltage, a primary electromagnetic field is produced, which induces eddy currents in the test weld 2.

The frequency of the sinusoidal voltage is chosen so that the high-frequency electromagnetic field produced by the superimposed eddy current transducer 1 would penetrate only into the surface layer of the test weld 2 without reaching a depth where a nugget 3 of test weld 2 may be located.

Eddy currents produce a secondary high-frequency electromagnetic field which, interacting with the primary high-frequency electromagnetic field, forms a resultant high-frequency electromagnetic field whose phase of intensity depends upon the conductivity of the material, i.e. upon the material structure of the surface layer of the test weld 2.

The resultant high-frequency electromagnetic field acts upon the superimposed transducer 1 varying its parameters according to the weld quality.

The phase of the resultant high-frequency electromagnetic field intensity is measured and translated into a voltage proportional thereto.

Thereupon, the frequency of the sinusoidal voltage powering the superimposed eddy current transducer 1 is varied, this frequency being chosen to be a lower value.

The frequency of the sinusoidal voltage is chosen so that a primary low-frequency electromagnetic field produced by the superimposed eddy current transducer 1 would penetrate to a depth where the nugget 3 of the test weld 2 may be located.

The primary low-frequency electromagnetic field induces eddy currents in the test weld 2.

Eddy currents produce a secondary low-frequency electromagnetic field which, interacting with the primary low-frequency electromagnetic field, forms a resultant low-frequency electromagnetic field whose phase of intensity depends upon the conductivity, i.e. upon the structure of the surface layer as well as of the nugget 3 of the test weld 2.

The resultant low-frequency electromagnetic field acts upon the superimposed eddy current transducer 1 varying its parameters dependently upon the weld quality.

The phase of the resultant low-frequency electromagnetic field is measured and is translated into the voltage proportional thereto.

Thereupon, the voltage obtained due to the action of the primary high-frequency electromagnetic field on the test weld 2 is compared with the voltage obtained due to the action of the primary low-frequency electromagnetic field on the test weld.

When the weld nugget is of high quality, the structures of the material in the surface layer and in the zone of the weld nugget 3 are different, and the material in these zone has different conductivities. If the difference between the voltage corresponding to the surface layer and the voltage corresponding to the zone of the weld nugget 3 exceeds a preset value $U_o$ which corresponds to the reference weld quality, the weld 2 is of high quality, and if this difference is below a preset value, the test weld is of poor quality.

Shown in the graph of FIG. 1 are a curve 4 corresponding to a voltage $U_1$ proportional to the phase of the resultant high-frequency electromagnetic field intensity, and a curve 5 corresponding to a voltage $U_2$ proportional to the phase of the resultant low-frequency electromagnetic field intensity, the abscissa being the time, t, over which testing is performed, while on the ordinate the voltage, U, is plotted.

It is evident from the graph that, since the voltage difference $\Delta U = U_1 - U_2$ is greater than $U_o$, the test weld 2 is of high quality.

Figure 2:
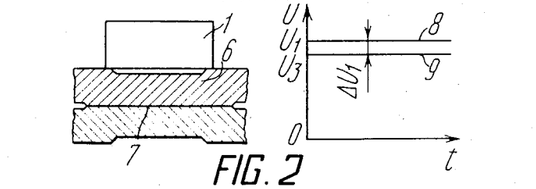
FIG. 2 is a cross-sectional view of another kind of the spot weld, with the superimposed eddy current transducer, and a graph representing the output signal of the superimposed eddy current transducer versus the time over which testing is performed, according to the invention.

FIG. 2 shows a kind of a spot weld wherein a test spot weld has no nugget.

The absence of the weld nugget determines little difference between the structures of the surface layer and a zone 7 wherein the nugget of a spot weld of high quality should be located.

Accordingly, conductivities of these zones differ insignificantly.

The voltage obtained due to the action of the primary high-frequency electromagnetic field on the test weld 6 is only slightly different from that obtained due to the action of the primary low-frequency electromagnetic field on the test weld 6.

Referring to a curve 8, it can be seen that, since the structure of the surface layer in the test weld 6 is similar to that in the test weld 2, the voltage corresponding to this zone in the test weld 6 is equal to $U_1$.

Referring now to a curve 9, it can be seen that the voltage $U_3$ corresponding to the zone 7 is only slighty different from the voltage $U_1$. The difference $\Delta U_1 = U_1 - U_3$ is smaller than $U_o$, i.e. the test weld 6 is of poor quality.

Figure 3:
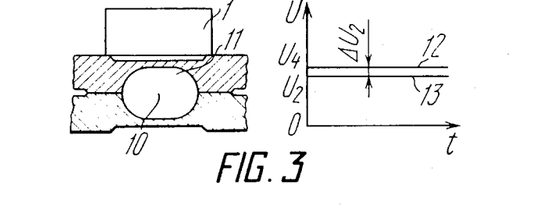
FIG. 3 is a cross-sectional view of still another kind of the spot weld with the superimposed eddy current transducer and a graph representing the output signal of the superimposed eddy current transducer versus the time over which testing is performed, according to the invention.

FIG. 3 shows another kind of the spot weld, wherein a nugget 10 of a test spot weld 11 reaches the surface of the test weld 11.

Since the nugget 10 extends substantially across the whole width of the test weld 11, there is a little difference in structures of the surface layer and the nugget 10.

Accordingly, conductivities of these zones differ insignificantly.

The voltage obtained due to the action of the primary high-frequency electromagnetic field on the test weld 11 is only slightly different from that obtained due to the action of the primary low-frequency electromagnetic field on the test weld 11.

A curve 12 corresponds to the voltage $U_4$ proportional to the phase of the resultant high-frequency electromagnetic field intensity, and a curve 13 corresponds to the voltage $U_2$ proportional to the phase of the resultant low-frequency electromagnetic field intensity.

Since the structure of the zone wherein the nugget 10 of the test weld 11 is located is similar to that wherein the nugget 3 of the test weld 2 is located, the voltage corresponding to the zone of the nugget 10 is equal to $U_2$.

It can be seen from the curve 12 that the voltage $U_4$ corresponding to the surface layer of the test weld 11 is only slightly different from the voltage $U_2$.

The difference $\Delta U_2 = U_4 - U_2$ is smaller than $U_o$, i.e. the test weld 11 is of poor quality.

Given below are the examples of the embodiments of the proposed method of and of the apparatus for nondestructive testing of spot welds under various conditions. The compositions of the steels used in the examples are as follows:

|  | C, % | Mn, % | Si, % | P, % | S, % |
|---|---|---|---|---|---|
| Steel 15 KP | 0.12–0.20 | 0.35–0.65 | 0.17–0.37 | 0.045 | 0.040 |
| Steel 08 KP | 0.05–0.11 | 0.25–0.50 | 0.30 | 0.040 | 0.40 |

EXAMPLE 1

| Brand of the test weld material | 15 KP steel with DC magnetizing |
|---|---|
| Thickness of the test weld material | 3 + 3 mm |
| Frequency of the high-frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_1$ | 0.26 V |
| Voltage obtained due to the action of the primary low-frequency electromagnetic field on the test weld, $U_2$ | 0,10 V |
| Voltage difference, $\Delta U = U_1 - U_2$ | 0.16 V |

Since $\Delta U$ is greater than $U_o$, the test weld is of high quality and corresponds to the spot weld shown in FIG. 1.

EXAMPLE 2

| | |
|---|---|
| Brand of the test weld material | 15 KP steel with DC magnetizing |
| Thickness of the test weld material | 3 + 3 mm |
| Frequency of the high-frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_1$ | 0.26 V |
| Voltage obtained due to the action of the primary low-frequency electromagnetic field on the test weld, $U_3$ | 0.22 V |
| Voltage difference $\Delta U_1$ between the voltage $U_1$ and the voltage $U_3$ | 0.04 V |

Since $\Delta U_1$ is smaller than $U_o$, the test weld is of poor quality and corresponds to the spot weld shown in FIG. 2.

EXAMPLE 3

| | |
|---|---|
| Brand of the test weld material | 15 KP steel with DC magnetizing |
| Thickness of the test weld material | 3 + 3 mm |
| Frequency of the high-frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_4$ | 0.15 V |
| Voltage obtained due to the action of the primary low-frequency electromagnetic field on the test weld, $U_2$ | 0.10 V |
| Voltage difference $\Delta U_2$ between the voltage $U_4$ and the voltage $U_2$ | 0.05 V |

Since $\Delta U_2$ is smaller than $U_o$, the test weld is of poor quality and corresponds to the spot weld shown in FIG. 3.

EXAMPLE 4

| | |
|---|---|
| Brand of the test weld material | 08 KP steel with DC magnetizing |
| Thickness of the test weld material | 3 + 3 mm |
| Frequency of the high frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_1$ | 0.6 V |
| Voltage obtained due to the action of the primary low-frequency electromagnetic field on the test weld, $U_2$ | 0.36 V |
| Voltage difference $\Delta U$ between the voltage $U_1$ and the voltage $U_2$ | 0.24 V |

Since $\Delta U$ is greater than $U_o$, the test weld is of high quality and corresponds to the spot weld shown in FIG. 1.

EXAMPLE 5

| | |
|---|---|
| Brand of the test weld material | 08 KP steel with DC magnetizing |
| Thickness of the test weld material | 3 + 3.5 mm |
| Frequency of the high-frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_1$ | 0.68 V |
| Voltage obtained due to the action of the primary low-frequency electromagnetic field on the test weld, $U_3$ | 0.63 V |
| Voltage difference $\Delta U_1$ between the voltage $U_1$ and the voltage $U_3$ | 0.05 V |

Since $\Delta U_1$ is smaller than $U_o$, the test weld is of poor quality and corresponds to the spot weld shown in FIG. 2.

EXAMPLE 6

| | |
|---|---|
| Brand of the test weld material | 08 KP steel with DC magnetizing |
| Thickness of the test weld material | 3 + 3.5 mm |
| Frequency of the high-frequency sinusoidal voltage | 120 kHz |
| Frequency of the low-frequency sinusoidal voltage | 3 kHz |
| Preset voltage, $U_0$ | 0.10 V |
| Voltage obtained due to the action of the primary high-frequency electromagnetic field on the test weld, $U_4$ | 0.40 V |
| Voltage obtained due to the action of the primary low-frequency electromagnetic field on the test weld, $U_2$ | 0.36 V |
| Voltage difference $\Delta U_2$ between the voltage $U_4$ and the voltage $U_2$ | 0.04 V |

Since $\Delta U_2$ is smaller than $U_o$, the test weld is of poor quality and corresponds to the spot weld shown in FIG. 3.

In order to distinguish a type of defect of the low-quality spot welds, i.e. to reveal sticking-type spot welds and through penetration-type spot welds, the superimposed eddy current transducer 1 (FIG. 4) is installed on the low-quality spot weld 11 in the immediate vicinity to the nugget 10. The superimposed eddy current transducer 1 powered by a sinusoidal high-frequency voltage generates a primary high-frequency electromagnetic field inducing eddy currents in the test weld 11.

Figure 4:
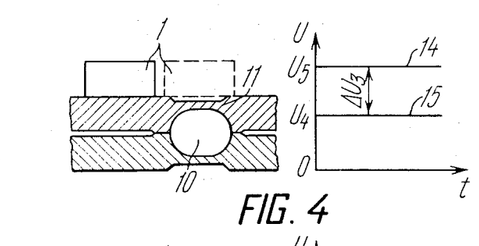
FIG. 4 is a cross-sectional view of a spot weld with a superimposed eddy current traducer, and a graph representing the output signal of the superimposed eddy current transducer versus the time over which testing is performed, according to the invention.

The frequency of the sinusoidal voltage is chosen so as to provide penetration of the primary high-frequency electromagnetic field produced by the superimposed eddy current transducer 11 but only into the surface layer of the test weld 11 without reaching a depth at which the nugget of the high-quality spot weld should be located.

Eddy currents produce a secondary high-frequency electromagnetic field which, interacting with the primary high-frequency electromagnetic field, forms a resultant high-frequency electromagnetic field whose phase of intensity is determined by the conductivity of the material, viz. by the structure of the surface layer material in the zone disposed in the immediate vicinity to the weld nugget.

The resultant high-frequency electromagnetic field acts upon the superimposed eddy current transducer 1 varying its parameters according to the conductivity of the material in this zone.

Next, the phase of the resultant high-frequency electromagnetic field intensity is measured and transformed into a voltage proportional thereto.

Thereupon, the intensity produced by the primary high-frequency electromagnetic field acting on the test weld 11 in the zone located in the immediate vicinity to the weld nugget is quantitatively compared with the intensity due to the action of the primary high-frequency electromagnetic field on the test weld 11 in the nugget zone, whereby the type of the spot weld defect is discerned.

When the weld nugget is of poor quality, the structure of the material of the surface layer disposed in the immediately vicinity to the weld nugget zone differs from the structure of the material of the surface layer disposed directly in the weld nugget zone. This results in that the materials in said zones have different conductivities. If the difference between the voltage corresponding to the surface layer disposed in the immediate vicinity to the weld nugget zone and the voltage corresponding to the surface layer disposed directly in the weld nugget zone is above the preset value $U_o$, the test spot weld suffers from a through-penetration the defect, whereas if said difference is lower than the preset value $U_o$, the test spot weld suffers from a sticking-type defect.

FIG. 4 shows a kind of the spot weld 11 with the nugget 10 extending to the surface of the spot weld 11. The extension of the weld nugget 10 substantially throughout the whole thickness of the test spot weld 11 results in a marked difference in the structures of the surface layer disposed in the immediate vicinity to the weld nugget zone and of the surface layer disposed directly in the weld nugget zone.

Accordingly, conductivities of said zoned differ significantly.

The graph of FIG. 4 shows voltage U plotted versus time t. A curve 14 corresponds to a voltage $U_5$ proportional to the phase value of the intensity of the resultant high-frequency electromagnetic field produced in the surface layer disposed in the immediate vicinity to the weld nugget zone, while a curve 15 corresponds to a voltage $U_4$ proportional to the phase value of the intensity of the resultant high-frequency electromagnetic field applied to the surface layer disposed directly in the weld nugget zone.

It is clear from the graph that since the voltage difference $\Delta U_3 = U_5 - U_4$ is greater than $U_o$, the test weld 11 has a defect of a through-penetration type.

Figure 5:
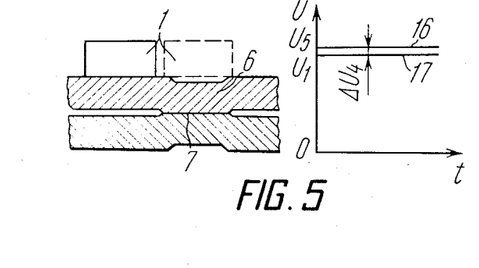
FIG. 5 is a cross-sectional view of a spot weld with a superimposed eddy current transducer, and a graph representing the output signal of the superimposed eddy current transducer versus the time over which testing is performed, according to the invention.

FIG. 5 shows the spot weld 6 free from the weld nugget.

The absence of the weld nugget determines a little difference between the structures of the surface layer disposed in the immediate vicinity to the the weld nugget zone and of the surface layer disposed directly in the weld nugget zone.

Accordingly, conductivities of these zones differ insignificantly.

Shown on the grapah of FIG. 5 are a curve 16 corresponding to voltage $U_5$ proportional to the phase of the intensity of the resultant high-frequency electromagnetic field produced in the surface layer disposed in the immediate vicinity to the weld nugget zone, and a curve 17 corresponding to voltage $U_1$ proportional to the phase of the intensity of the resultant high-frequency electromagnetic field produced in the surface layer disposed directly in the weld nugget zone.

It is evident from the graph that since the voltage difference $\Delta U_4 = U_5 - U_1$ is smaller than $U_o'$, the test weld 6 suffers from a sticking-type defect.

Given below are the examples of the embodiments of the proposed method of nondestructive testing of spot welds.

EXAMPLE 7

| | |
|---|---|
| Brand of the test weld material | 15 KP steel with DC magnetizing |
| Thickness of the test weld material | 3 + 3 mm |
| Frequency of the high-frequency sinusoidal voltage | 120 kHz |
| Preset voltage, $U_0$ | 0.10 V |
| Voltage obtained due to the action of the primary high-frequency electromagnetic field on the weld nugget zone, $U_1$ | 0.26 V |
| Voltage obtained due to the action of the primary high-frequency electromagnetic field on a portion disposed in the immediate vicinity to the weld nugget zone, $U_5$ | 0.31 V |
| Voltage difference $\Delta U_4 = U_5 - U_1$ | 0.05 V |

Since $\Delta U_4$ is smaller than $U_o$, the low-quality spot weld has a sticking-type defect.

EXAMPLE 8

| | |
|---|---|
| Brand of the test weld material | 15 KP steel with DC magnetizing |
| Thickness of the test weld material | 3 + 3 mm |
| Frequency of the high-frequency sinusoidal voltage | 120 kHz |
| Preset voltage, $U_0$ | 0.10 V |
| Voltage obtained due to the action of the primary high-frequency electromagnetic field on the test spot weld in the weld nugget zone, $U_3$ | 0.15 V |
| Voltage obtained due to the action of the primary high-frequency electromagnetic field on a portion of the test spot weld, disposed in the immediate vicinity to the weld nugget zone, $U_5$ | 0.31 V |
| Voltage difference $\Delta U_3 = U_5 - U_4$ | 0.16 V |

Since $\Delta U_3$ is greater than $U_o$, the test spot weld of low quality suffers from a sticking-type defect.

EXAMPLE 9

| Brand of the test weld material | 08 KP steel with DC magnetizing |
|---|---|
| Thickness of the test weld material | 3 + 3.5 mm |
| Frequency of the high-frequency sinusoidal voltage | 120 kHz |
| Preset voltage, $U_0$ | 0.10 V |
| Voltage obtained due to the action of the primary high-frequency electromagnetic field on the test spot weld in the weld nugget zone, $U_1$ | 0.68 V |
| Voltage obtained due to the action of the primary high-frequency electromagnetic field on a portion of the test spot weld, disposed in the immediate vicinity to the weld nugget zone $U_5$ | 0.74 V |
| Voltage difference, $\Delta U_4 = U_5 - U_1$ | 0.06 V |

Since $\Delta U_4$ is smaller than $U_o$, the test spot weld of poor quality suffers from a sticking-type defect.

EXAMPLE 10

| Brand of the test weld material | 08 KP steel with DC magnetizing |
|---|---|
| Thickness of the test weld material | 3 + 3.5 mm |
| Frequency of the high-frequency sinusoidal voltage | 120 kHz |
| Preset voltage, $U_0$ | 0.10 V |
| Voltage obtained due to the action of the primary high-frequency electromagnetic field on the test spot weld in the weld nugget zone, $U_4$ | 0.40 V |
| Voltage obtained due to the action of the primary high-frequency electromagnetic field on a portion of the test spot weld, disposed in the immediate vicinity to the nugget zone, $U_5$ | 0.74 V |
| Voltage difference, $\Delta U_3 = U_5 - U_4$ | 0.34 V |

Since $\Delta U_3$ is greater than $U_o$, the test spot weld of poor quality suffers from a through-penetration type defect.

The apparatus realizing the method described hereinabove comprises a high-frequency measuring channel 18 (FIG. 6) including a high-frequency signal generator 19, an unbalanced bridge circuit 20 and a phase detector 21, connected in series, and a low-frequency measuring channel 22 including a low-frequency signal generator 23, an unbalanced bridge circuit 24 and a phase detector 25, connected in series. The output of the phase detector 21 is connected to the input of a memory unit 26 having its output connected to a first signal input of a comparator 27 whose output is connected to an indicator 28.

Figure 6:
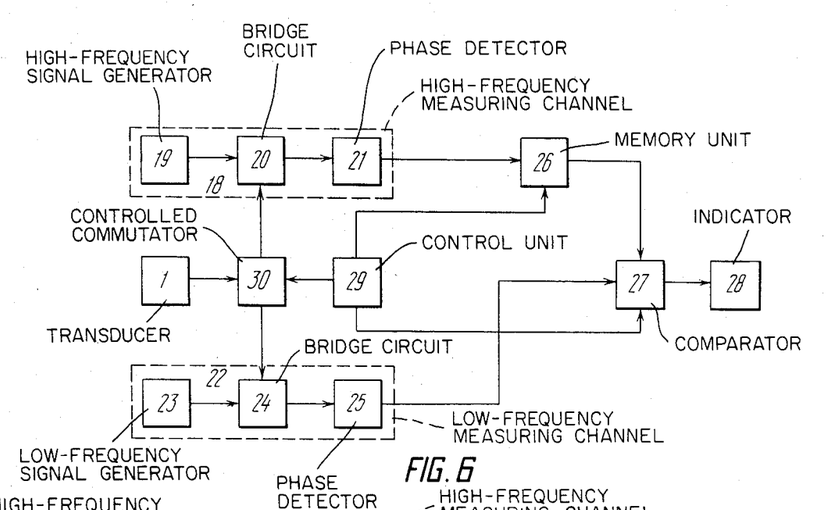
FIG. 6 is a block-diagram of an apparatus realizing a method of nondestructive testing of spot welds, according to the invention.

The output of the phase detector 25 is connected to a second signal input of the comparator 27.

A control input of the comparator 27 is connected to one of the outputs of a control unit 29. A second output of the control unit 29 is connected to a control input of the memory unit 26. A third output of the control unit 29 is connected to a control input of a controlled commutator 30.

The superimposed eddy current transducer 1 is connected to an input of the controlled commutator 30 whose outputs are respectively connected to the unbalanced bridge circuit 20 and to the unbalanced bridge circuit 24.

Figure 7:
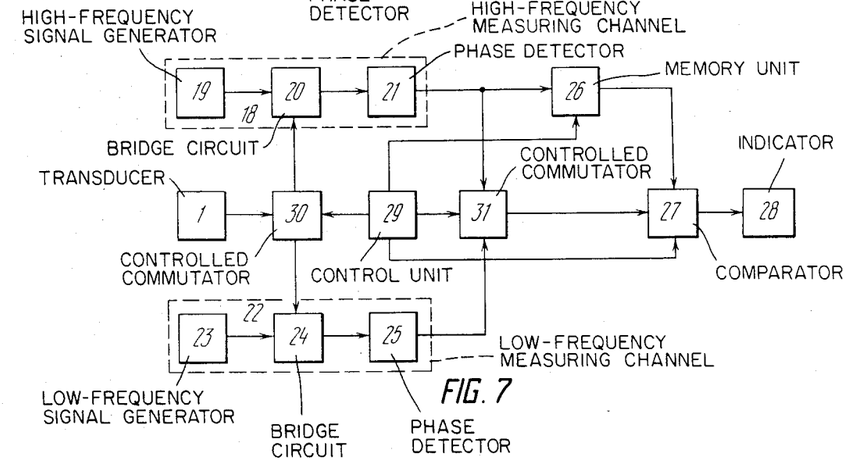
FIG. 7 is a block-diagram of another embodiment of the apparatus realizing a method of nondestructive testing of spot welds, according to the invention.

In one embodiment shown in FIG. 7, the output of the phase detector 21 is connected to one of the inputs of a controlled commutator 31, while the output of the phase detector 25 is connected to another input of the controlled commutator 31. A control input of the controlled commutator 31 is connected with a fourth output of the control unit 29. The output of the controlled commutator 31 is connected to a second signal input of the comparator 27.

The proposed apparatus realizing the method of nondestructive testing of spot welds operates as follows.

The superimposed eddy current transducer 1 (FIG. 1) is placed over the test spot weld 2.

The control unit 29 (FIG. 6) is energized to supply a control signal to the controlled commutator 30 which switches the coil of the superimposed eddy current transducer 1 into the unbalanced bridge circuit 20 included into the high-frequency measuring channel 18. The sinusoidal high-frequency voltage from the high-frequency signal generator 19 is applied to the unbalanced bridge circuit 20.

The unbalanced bridge circuit 20 is adjusted so that the phase of the output voltage is independent from the size of the lift-off formed between the superimposed eddy current transducer 1 and the test spot weld, and is determined only by variations in the conductivity of the test region, which in turn is dependent upon the weld quality.

The current flowing through the coil of the superimposed eddy current transducer 1 produces a primary high-frequency electromagnetic field which induces in the surface layer of the test weld 2 (FIG. 1) eddy currents producing a secondary high-frequency electromagnetic field.

The resultant high-frequency electromagnetic field acts on the coil of the superimposed eddy current transducer 1, thus varying its impedance according to the value of the conductivity of the material in the zone of eddy currents.

From the output of the unbalanced bridge circuit 20 (FIG. 6) the voltage whose phase of value is dependent upon the conductivity of the material in the zone of action of the primary high-frequency electromagnetic field produced by the superimposed eddy current transducer 1, is applied to the input of the phase detector 21.

Simultaneously with the supply of the control signal from the control unit 29 to the controlled commutator 30, a signal is supplied from the control unit 29 to the control input of the memory unit 26. From the output of the phase detector 21 the voltage proportional to the phase value of the output voltage of the unbalanced bridge circuit 20 viz. to the conductivity of the material in the surface layer of the test weld 2 (FIG. 1), is fed to the input of the memory unit 26 (FIG. 6) wherein the voltage is stored in an analog form.

After the voltage is stored in the memory unit 26, the supply of the signal to its control input from the control unit 29 is cut off. Simultaneously with the cut-off of signal supply to the control input of the memory unit 26 from the control unit 29, the signal from the latter is supplied to the control input of the comparator 27 and to the controlled commutator 30.

After the signal is fed to the controlled commutator 30, the coil of the superimposed eddy current transducer 1 is disconnected from the unbalanced bridge circuit 20 and switched into the unbalanced bridge circuit 24 included into the low-frequency measuring channel 22.

The low-frequency sinusoidal voltage is applied from the low-frequency signal generator 23 to the unbalanced bridge circuit 24.

The unbalanced bridge circuit 24 is adjusted so that the phase of the output voltage is independent of the size of the lift-off formed between the superimposed eddy current transducer 1 and the test spot weld, and is determined only by variations in the conductivity in the test region, which, in turn, is dependent upon the weld quality.

Current flowing through the coil of the superimposed eddy current transducer 1 produces a primary low-frequency electromagnetic field which induces eddy currents in the zone of the weld nugget 3 (FIG. 1) of the test weld 2. Eddy currents produce, in turn, a secondary low-frequency electromagnetic field.

The resultant low-frequency electromagnetic field acts on the coil of the superimposed eddy current transducer 1, thus varying its impedance according to the conductivity of the material in the zone of eddy currents.

From the output of the unbalanced bridge circuit 24 (FIG. 6) the voltage whose phase depends upon the conductivity of the material in the zone of action of the primary low-frequency electromagnetic field produced by the superimposed eddy current transducer 1, is applied to the input of the phase detector 25.

From the output of the phase detector 25 the voltage proportional to the phase of the output voltage of the unbalanced bridge circuit 24 viz. to the conductivity of the material in the weld nugget zone (FIG. 1) is fed to the second signal input of the comparator 27 (FIG. 6), the voltage from the memory unit 26 being applied to the first signal input thereof.

The comparator 27 compares the signals supplied from the phase detector 25 and from the memory unit 26, whereupon the difference of this signals is applied to the indicator 28.

The spot weld is of high quality if the difference between the signals on the display of the indicator 28 exceeds a preset value.

If the difference between the signals on the display of the indicator 28 is below a preset voltage value, the spot weld is of poor quality.

Then the supply of signals from the control unit 29 to the controlled commutator 30 and to the control input of the comparator 27 is cut off.

The superimposed eddy current transducer 1 is disconnected from the unbalanced bridge circuit 24, the supply of the signal difference from the output of the comparator 27 to the indicator 28 is cut off, and the cycle of testing residing only in distinguishing high-quality spot welds from low-quality spot welds comes to its end.

In case it is necessary to recognize a type of defect of the low-quality spot welds, the superimposed eddy current transducer 1 (FIG. 7) is installed on the test article in the immediate vicinity to the weld. The control unit 29 is energized thus supplying a signal to the control input of the controlled commutator 30 which switches the coil of the superimposed eddy current transducer 1 into the unbalanced bridge circuit 20. At a time, signals from the control unit 29 are applied to the control inputs of the controlled commutator 31 and of the comparator 27. In doing so, the controlled commutator 31 connects the output of the phase detector 21 with the second signal input of the comparator 27.

The current flowing through the coil of the superimposed eddy current transducer 1 produces a primary high-frequency electromagnetic field inducing eddy currents in the surface layer of the test weld in the zone disposed in the immediate vicinity to the weld nugget zone. The resultant high-frequency electromagnetic field acts on the coil of the superimposed eddy current transducer 1, thus varying its impedance according to the conductivity of the material in said zone.

From the output of the unbalanced bridge circuit 20, the voltage is fed to the input of the phase detector 21 initiating at its output the voltage proportional to the phase of the output voltage of the unbalanced bridge circuit 20.

From the phase detector 21, the output voltage is fed to the second signal input of the comparator 27 through the controlled commutator 31.

The comparator 27 compares the signals supplied from the memory unit 26 and from the phase detector 21, the signal being recorded in the memory unit 26 when the coil of the superimposed eddy current transducer 1 installed in the weld nugget zone was included into the unbalanced bridge circuit 20.

Then the signal difference is applied to the indicator 28.

If the difference between the signals on the display of the indicator 28 is above a preset voltage value, the spot weld suffers from a through penetration type defect. If the signal difference is below a preset voltage value, the spot weld suffers from a sticking-type defect.

Next, the control unit 29 cuts off supply of the signal to the controlled commutator 31 and to the input of the comparator 27. The supply of the signal difference from the output of the comparator 27 is cut off, and the cycle of testing comes to its end.

Thus, the present invention makes it possible to carry out continuous nondestructive testing of spot welds and to reveal defective spot welds.

Besides, the invention makes it possible to perform testing without previous adjustment on a reference weld and to improve the reliability of testing due to elimination of such interfering factors as:
  variations in the chemical composition of the test weld material;
  variations in the structure of the test weld material; and
  variations in the environmental conditions such as an ambient temperature.

What is more, the present invention makes it possible to reveal a type of defect of the weld nugget, namely to distinguish spot welds with a sticking-type defect and spot welds with a through penetration type defect.

Metallic structures in which the spot welds suffer from a through penetration type defect can be used in operation under restricted cycles of dynamic load, while metallic structures in which the spot welds suffer from a sticking-type defect must be subjected to repeated welding for rectifying this defect, thus reducing a number of rejected metallic structures.

From the spicific embodiments of the present invention considered hereinabove, it is readily apparent to those skilled in the art that all the objects and advantages of the invention can be accomplished within the scope of the appended claims. It is also apparent that insignificant changes in the steps of the method and in the construction of the apparatus realizing this method can be made without departing from the spirit of the invention. All these insignificant changes are considered to be within the spirit and scope of the invention as defined in the claims below.

What is claimed is:

1. An apparatus for nondestructive testing of spot welds by comparing eddy currents induced in the weld zone by means of high- and low-frequency electromagnetic fields, comprising:

a high-frequency measuring channel including:
a high-frequency signal generator for generating a high-frequency electromagnetic field that penetrates only the surface area of the weld zone and having an output;
an unbalanced bridge circuit having an input, an output, and a control input, said input of said unbalanced bridge circuit being connected to said output of said high-frequency signal generator;
a phase detector having an input and an output, said input of said phase detector being connected to said output of said unbalanced bridge circuit of said high-frequency measuring channel;

a low-frequency measuring channel comprising:
a low-frequency signal generator for generating a low frequency electromagnetic field that penetrates the interior of the weld zone and having an output;
an unbalanced bridge circuit having an input, an output and a control input, said input of said unbalanced bridge circuit being connected to said output of said low-frequency signal generator;
a phase detector having an input and an output, said input of said phase detector being connected to said output of said unbalanced bridge circuit of said low-frequency measuring channel;

an eddy current transducer;

a controlled commutator having a signal input connected to said eddy current transducer, a control input, an output connected to said control input of said unbalanced bridge circuit of said high-frequency measuring channel, and an output connected to said control input of said unbalanced bridge circuit of said low-frequency measuring channel;

a controlled memory unit having a signal input, a control input, and an output, said signal input of said controlled memory unit being connected to said output of said phase detector of said high-frequency measuring channel;

a controlled comparator having a first signal input, a second signal input, a control input, and an output, the first signal input of said controlled comparator being connected to said output of said controlled memory unit, said second input of said controlled comparator being connected to said output of said phase detector of said low-frequency measuring channel;

an indicator having an input connected to said output of said controlled comparator;

a control unit having three control outputs connected respectively to said control input of said controlled commutator, to said control input of said controlled comparator, and to said control input of said controlled memory unit, said control unit adapted to generate alternately signals simultaneously applied to said control input of said controlled commutator to connect said eddy current transducer into said unbalanced bridge circuit of said high-frequency measuring channel, and to said control input of said memory unit for storing the output signal of said phase detector of said high-frequency measuring channel, and signals simultaneously applied to said control input of said controlled commutator to connect said eddy current transducer into said unbalanced bridge circuit of said low-frequency measuring channel, and to said control input of said controlled comparator to compare the signal stored in said controlled memory unit with the signal of said phase detector of said low-frequency measuring channel.

2. An apparatus as defined in claim 1, wherein said control unit is provided with a fourth control output, and the apparatus is further provided with a second controlled commutator connected to said output of said phase detector of said high-frequency measuring channel, to said output of said phase detector of said low frequency measuring channel, and to said fourth control output of said control unit, generating signals used to connect simultaneously said eddy current transducer to said unbalanced bridge circuit of said high-frequency measuring channel, to connect said phase detector of said high-frequency measuring channel to said second signal input of said controlled comparator, and to compare the signal from said phase detector of said high-frequency measuring channel with the signal stored in said controlled memory unit.

* * * * *